United States Patent [19]
Andersen

[11] Patent Number: 5,360,440
[45] Date of Patent: Nov. 1, 1994

[54] IN SITU APPARATUS FOR GENERATING AN ELECTRICAL CURRENT IN A BIOLOGICAL ENVIRONMENT

[75] Inventor: Erik Andersen, Roskilde, Denmark

[73] Assignee: Boston Scientific Corporation, Watertown, Mass.

[21] Appl. No.: 847,911

[22] Filed: Mar. 9, 1992

[51] Int. Cl.⁵ .............................................. A61N 1/00
[52] U.S. Cl. ...................................... 607/116; 607/75
[58] Field of Search ................. 128/784, 785; 606/191, 606/194, 195, 198; 604/21; 607/75, 115, 116

[56] References Cited

U.S. PATENT DOCUMENTS

| | | | |
|---|---|---|---|
| 4,776,337 | 10/1988 | Palmaz | 606/194 |
| 4,886,505 | 12/1989 | Haynes et al. | 128/784 |
| 4,922,905 | 5/1990 | Strecker | 606/195 |
| 5,108,417 | 4/1992 | Sawyer | 606/191 |
| 5,195,529 | 3/1993 | Malkamäki | 128/725 |

FOREIGN PATENT DOCUMENTS

| | | | |
|---|---|---|---|
| 8607543 | 12/1986 | WIPO | 128/785 |

OTHER PUBLICATIONS

Lerner et al., "Miniature Implantable Tantalum/Tantalum Oxide Stimulating Electrodes" IEEE vol. BME-29 No. 4 Apr. 1982.

B. Nordenstrom, Biologically Closed Electric Circuits, (Nordic Medical Publications, 1983).

*Primary Examiner*—Lee S. Cohen
*Assistant Examiner*—Jeffrey R. Jastrzab
*Attorney, Agent, or Firm*—Pearson & Pearson

[57] ABSTRACT

An apparatus for the in situ generation of an electrical current in a biological environment characterized by including an electrolytic fluid. The apparatus comprises first and second electrodes of differing electrochemical potentials separated by an insulator. The apparatus is adapted to be implanted in the environment. The presence of the electrolytic fluid and formation of a current path by hyperplastic cells bridging the electrodes enables electrolysis to occur and a direct current to pass through the current path to impede hyperplastic cell growth.

35 Claims, 2 Drawing Sheets

IN SITU APPARATUS FOR GENERATING AN ELECTRICAL CURRENT IN A BIOLOGICAL ENVIRONMENT

BACKGROUND OF THE INVENTION

1. Field of the Invention

This invention generally relates to apparatus for producing an electric potential within a biological environment and more specifically to apparatus for the in situ generation of an electric current in that environment.

2. Description of Related Art

It is known that the application of an electric potential to selected portions in the human body or other biological environments can produce beneficial results. In some procedures, the electric potential produces a current through the selected portions of the body; in others it does not.

For example, the placement of a bimetal structure in the bloodstream constitutes an example of the use of a structure that produces an electrical potential without any current. Electrons migrate to one of the two metals that becomes a cathode and away from the other metal that becomes an anode. The resulting electrical field at the electrodes produces the beneficial result, namely the production of a positive surface charge on the anode that promotes blood clotting.

In accordance with other procedures, an external power source produces a current between spaced electrodes positioned in a biological environment. In one procedure, a platinum electrode, as an anode, is implanted percutaneously in a tumor and another platinum electrode, as a cathode, is implanted percutaneously in tissue at least one tumor diameter from the tumor. Current between the electrodes, generated when the external source is energized, has been shown to promote tumor regression. See B. Nordenström, Biologically Closed Electric Circuits (Nordic Medical Publications 1983).

In these and similar procedures, it is necessary to implant each electrode percutaneously, usually using radiographic procedures to assure accurate electrode positioning. Treatment sessions may last for extended times of an hour or more and may be painful to a patient. At the end of the session a surgeon removes the electrodes. If another treatment is necessary, the entire procedure is repeated.

There is also a class of tubular endoprostheses known as "stents" that are well known and have a variety of forms. A stent usually comprises a tubular, radially expanding structure that can be implanted in a vessel to engage and support secondary tissue and maintain vessel patency. Stents may be utilized in body canals, blood vessels, ducts and other body passages and cavities and the term "vessel" is meant to include all such passages and cavities. A stent delivery system typically includes a catheter that supports the stent in a compacted, or low profile, form for transport to a site of implantation. Any of a variety of mechanisms expand the stent radially into the surrounding tissue. After the catheter is removed, the stent retains its expanded shape.

United States Letters Patent No. 4,922,905 of Ernst P. Strecker for a "Dilation Catheter" describes the manufacture, construction and use of certain embodiments of such stents. Strecker's disclosed stent comprises a tubular structure that is knitted from metal or plastic filaments to form a tubular endoprosthesis having a wall of loosely interlocked loops. When a physician uses a stent delivery system to properly position the stent, an auxiliary expansion device expands the stent radially causing a plastic deformation of the filament material so the stent retains its expanded shape. My co-pending U.S. application Ser. No. 07/773,847 filed Oct. 9, 1991 for an "Impregnated Stent" discloses a self-expanding stent that does not require an auxiliary expansion device. In these and other stents the filament forms an open mesh wall so the stent has the fluid transport characteristics of a permeable membrane.

Open mesh stents positioned in a vessel proximate a tumor are subject to tumor incursion with consequential partial or full vessel and stent occlusion. If the mesh openings through the stent wall are reduced to 30 microns or less, the stent can prevent cell penetration and prevent occlusion. However, such a stent also has the fluid transport characteristics of an impermeable membrane, so it blocks the transfer of fluid from surrounding tissue into the vessel through the stent wall. In certain vessels, such as the bile duct and urinary tract, such stents can reduce flow rate of a fluid, such as bile or urine, into the vessel from surrounding tissue. These conditions promote fluid crystallization. As a result crystals can form in the vessel and stent and partially or ultimately fully occlude the vessel and stent. Thus, the selection of a conventional stent structure for implantation proximate a tumor is a compromise that must be made in the face of the antithetical problems of tumor incursion and crystal formation.

Notwithstanding the selection of a stent, occlusion eventually occurs either by tumor incursion or crystal formation. The conventional remedial action is to replace the stent or remove the occlusion. As will be apparent, any such remedial action requires traumatic surgery. In many situations patients will not be able to tolerate such remedial actions, so such procedures can not even be considered. Consequently the occlusion must remain.

It has been proposed to resolve the antithetical problems of tumor incursion and crystal formation by using open mesh stent in a variant of the Nordenström apparatus. The use of an open mesh stent solves the crystal problem. According to this proposal, the Nordenström apparatus would incorporate a metallic stent as one of the two electrodes. Externally applied power would generate a current between the electrodes to cause tumor regression and restore patency through the stent thus overcoming the tumor incursion or slowing the rate of tumor incursion. If this variant is used in a straightforward manner, the first step involves monitoring procedures for determining patency. As a next step, a surgeon implants the stent, second electrode and attendant conductors. The electrodes are energized. After treatment, the surgeon removes at least the second electrode and conductors.

It has been suggested that the stent and second electrode be implanted permanently with the conductors being led to a location where they can be accessed without major surgery. This would minimize patient trauma and facilitate repeated procedures. However, in many applications the difficulty in routing the conductors from the stent to a convenient connection site and the problems of leaving the second electrode proximate the tumor are not readily resolved.

SUMMARY

Therefore it is an object of this invention to provide a method and apparatus for generating electric currents in a biological environment.

Another object of this invention is to provide implantable apparatus for the in situ generation of an electrical current at a localized site.

Still another object of this invention is to provide apparatus for implantation in a vessel for generating, in situ and in response to the presence of hyperplastic cells, an electrical current for transfer in a path formed by the hyperplastic cells.

Yet another object of this invention is to provide a stent assembly that inhibits the incursion of hyperplastic cells, including tumors, in the area of the stent by means of the in-situ generation of an electric current.

Still yet another object of this invention is to provide a stent assembly that inhibits the incursion of hyperplastic cells including tumors, by means of the in-situ generation of an electric current and that minimizes the potential for crystal formation within the stent and vessel.

These and other objects and advantages of this invention are attained by an apparatus for the in situ generation of electrical current in a biological environment characterized by the presence of an electrolyte. The in situ generator contacts the electrolyte and has first, second and third layers of materials. The first and second layers are composed of electrically conductive materials having different electrochemical potentials. The third layer is intermediate and insulates the first and second layers. If hyperplastic cells in the biological environment bridge the first and second layers, they form a current path. When this occurs, the apparatus, through electrolysis, generates an electrical current in this current path that inhibits further hyperplastic cell growth.

In accordance with another aspect of this invention, a stent assembly for location proximate an area of existent or potential hyperplasia, such as at a tumor, comprises, as nested elements, an inner stent, an intermediate insulator and an outer stent. A conductive material with a first electrochemical potential forms the inner stent. A conductive material with a different electrochemical potential forms the outer stent. The intermediate insulator electrically isolates the inner and outer stents. When hyperplastic cells forming the tumor pass proximate to and bridge the central and outer stents, the hyperplastic cells form a conductive path for a current generated by electrolysis.

Still another aspect of this invention involves a method for generating current for transfer through hyperplastic cells in an environment including an electrolytic fluid. A positioning step locates a multiple layer structure having first and second layers of electrically conductive mesh formed of materials of different electrochemical potentials in a vessel proximate a site of existent hyperplastic cells or of potential hyperplastic cell growth. The layers are insulated from one another and react to the presence of a bridge of the hyperplastic cells therebetween and the electrolytic fluid by generating an electrical current. This current impedes further growth of the hyperplastic cells.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
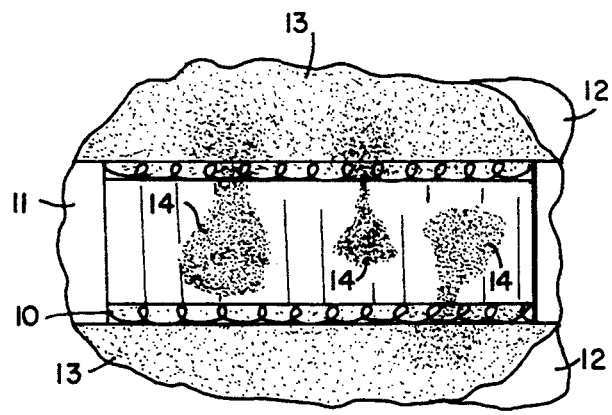
FIG. 1 is a diagram in cross-section of a prior art stent in tissue proximate a tumor with tumor incursions.

In many patients who are terminally ill with cancer, it is important to maintain vessel patency, even for a limited time, with minimal trauma. As previously described, the option of using a stent with the fluid characteristics of an impermeable membrane may not always be viable. However, as shown in FIG. 1, prior art open mesh stents are subject to tumor incursion. As known, these stents comprise a wire filament limited or otherwise formed into an open mesh with a cylindrical shape. Specifically, FIG. 1 depicts a prior art open mesh stent 10 located in a vessel 11 through surrounding tissue 12 and proximate a tumor 13. As the tumor 13 contacts the open mesh stent 10, tumor cells can migrate through the open mesh of the stent walls and produce tumor extensions or micro tumors 14 within the stent 10. As these micro tumors 14 grow, they partially occlude the vessel 11. Eventually they fully occlude the vessel 11 with the loss of function of the surrounding tissue 12. When this occurs, the resulting loss of function in the surrounding tissue may become life threatening. Under such circumstances the only practical alternative is to exchange the stent. As apparent, this requires the performance of a surgical procedure on a patient who may not be able to tolerate the procedure.

Figure 2:
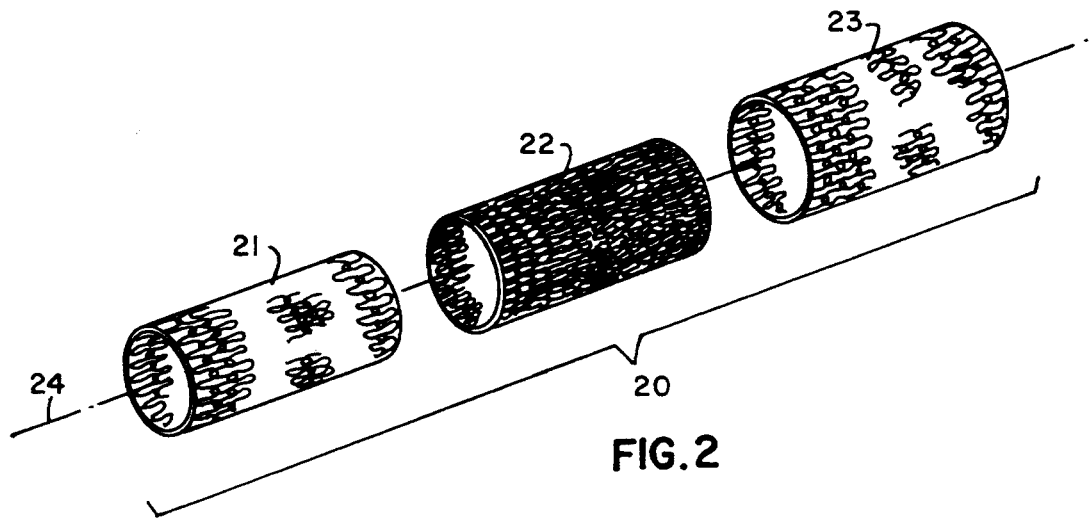
FIG. 2 is an exploded perspective view of the components of a stent assembly constructed in accordance with this invention.
Figure 3:
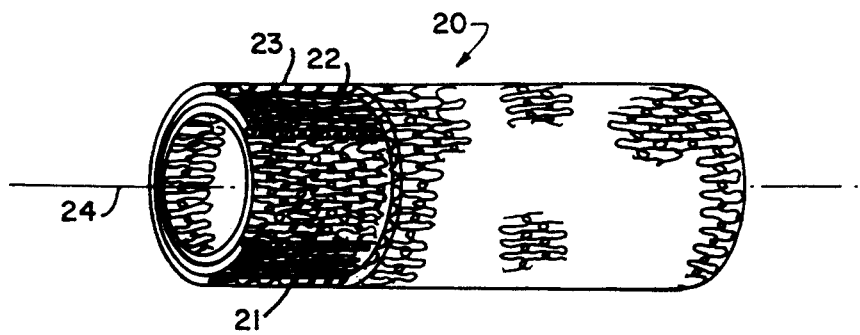
FIG. 3 is a perspective view, partially broken away, of the stent assembly shown in FIG. 2.

A stent assembly 20 shown in FIGS. 2 and 3 should maintain patency over a time interval of several months to a year or more without the need for iterative surgical processes. This stent assembly has the general form of an open-ended, closed wall structure and includes, as nested or concentric elements, an inner stent 21, an intermediate insulator 22 and an outer stent 23 that form a three-layer cylindrical structure in this specific embodiment. The materials and construction of the inner stent and outer stents 21 and 23 and the insulator 22 must meet a number of criteria. The primary criteria are that (1) the materials forming the inner and outer stents 21 and 23 have different electrochemical potentials and (2) the insulator 22 electrically isolates the inner and outer stents 21 and 23 from each other.

When a stent assembly 20 meeting these primary criteria is positioned in a vessel of the human body, it is immersed in an electrolytic fluid. For example, if the stent assembly 20 is located in a liver bile duct, the bile constitutes the electrolytic liquid. If the stent assembly 20 is located in the vascular network, blood constitutes the electrolytic liquid. If proximate cells from a structure that bridges portions of the inner and outer stents 21 and 23, the resulting electrolytic action produces an electric potential between the stents and a current flows through the bridging cell structure.

Other material selection and construction criteria depend upon the specific application for the stent assembly 20. For example selected materials should be compatible with the biological environment. That is, each material should be physiologically inert or neutral in the environment. As now will be apparent, either the inner stent 21 or the outer stent 23 acts as a cathode. Electrolysis will erode the anode and, if the material is physiologically neutral, any by-products of electrolysis should not have an adverse impact on the patient.

The stent acting as the cathode must have sufficient strength to be self-supporting independently of the other stent. Again, electrolysis eventually destroys the anode stent, so the overall strength of the cathode stent must be sufficiently strong to maintain vessel patency. Material selection, filament size and mesh size all control strength. Tantalum stents of a variety of filament sizes and mesh configurations are self-supporting in a variety of applications. Thus, tantalum is a preferred cathode material in a variety of applications.

The selected anode material and its construction must have an acceptable life expectancy. Once an anode material is selected, the mechanical design of the cathode controls life expectancy. For example, the selection of filament size and mesh size provides control over the life expectancy of an open-mesh stent. Iron is a preferred anode material. Silver is another possible anode material. It may have some beneficial healing properties, but the generated output voltage with a silver anode is less than with an iron anode. An anode of an aluminum-magnesium alloy will increase electrical output, but the stent assembly will have a life expectancy that is too short many applications.

The selection of mesh structure also impacts life expectancy and strength. This structure may take several well known forms. For example, each structure can comprise loosely interlocked loops that may be knitted as disclosed in the above-identified United States Letters Patent 4,922,905.

The intermediate insulator 22 can comprise any physiologically inert or neutral non-conductive material. Polymers, such as polyethylene, are suitable. The filament size and mesh size are not critical, except that the mesh size should be the smallest of the three elements thereby to assure the electrical isolation of the inner stent 21 and the outer stent 23.

Stent assemblies 20 of tantalum and iron have been immersed in liver bile for testing. Open-circuit potentials of up to 100 millivolts or more have been measured. When a load resistor of 10,000 ohms is connected, the stent assembly 20 still produces an output voltage up to 15 millivolts. The resulting current has been found sufficient to alter cell growth.

Figure 4:
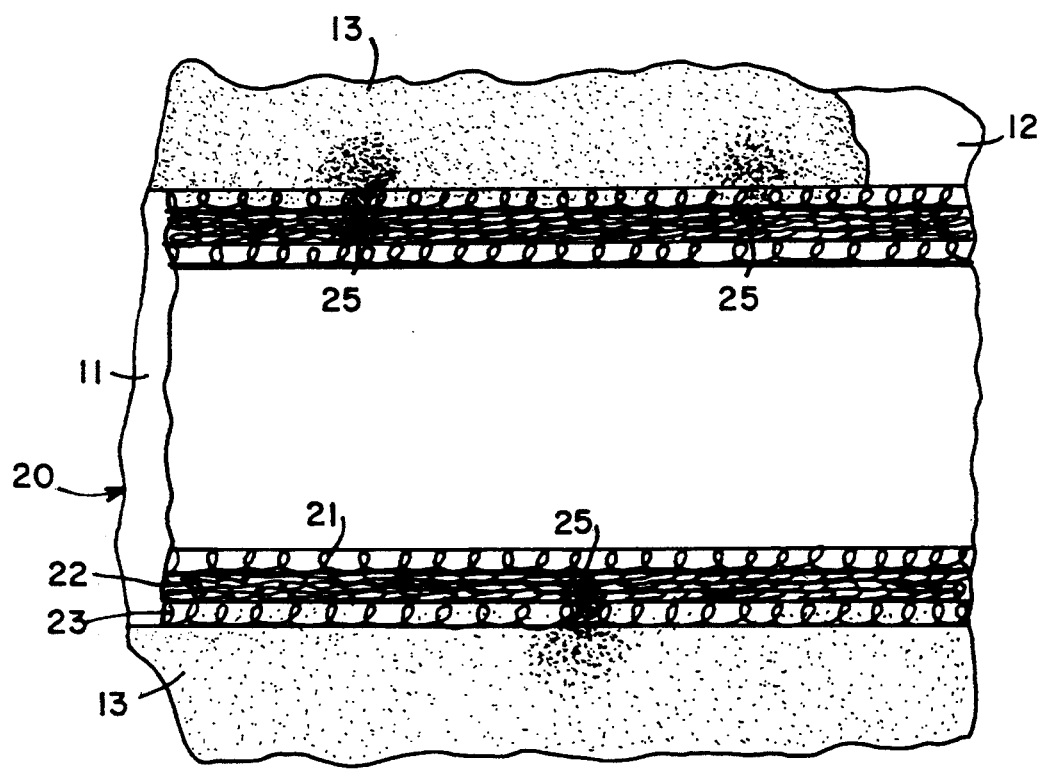
FIG. 4 is a sectional view of a stent assembly constructed in accordance with this invention located in a passageway proximate a tumor.

Animal tests with stents constructed in accordance with the specific embodiment of FIGS. 2 and 3, demonstrate that the location of this stent 20 adjacent a tumor 13, as shown in FIG. 4, maintains the patency of a vessel 11 for up to death due to carcinoma. Autopsies have demonstrated that the stents had maintained vessel patency through the progression of tumor growth. Apparently as tumor or other hyperplastic cells begin to transfer across the walls of the stent 20, they form a conductive path or bridge between the inner stent 21 and the outer stent 23. The resultant current, produced by electrolysis, disturbs the hyperplastic cell growth mechanism. Any micro tumors 25 that begin to form terminate at the inner stent 21. As a result the stent assembly 20 inhibits the formation of micro tumors even though the stet assembly 20 that comprises two foraminous electrodes and an intermediate foraminous insulator in the form of stents 21 and 23 and insulator 22, as a whole, has the fluid characteristics of a permeable membrane. This enables liquids, such as liver bile and urine, to pass normally into the vessel 11 from surrounding tissue 12 thereby minimizing the potential for crystal formation.

A further understanding of the construction and operation of a stent assembly embodiment of this invention can be attained by reference to the following specific example having the form shown in FIGS. 2 and 3 and being adapted for implantation in a liver bile duct.

| Element Parameter | Stent Elements | | |
|---|---|---|---|
| | Central Stent 21 | Insulator 22 | Outer Stent 23 |
| Material | Tantalum | Polyethylene | Iron |
| Filament Diameter | 0.1 mm | .25 mm | .125 mm |
| Loop Size | 6 loops 2 × 2 mm | 8 loops <1.7 mm | 6 loops 2.1 mm |
| Outer Diameter Expanded | 7–8 mm | 7–8 mm | 8 mm |
| Other Criteria | | Must keep 2 stents apart | |

Figure 5:
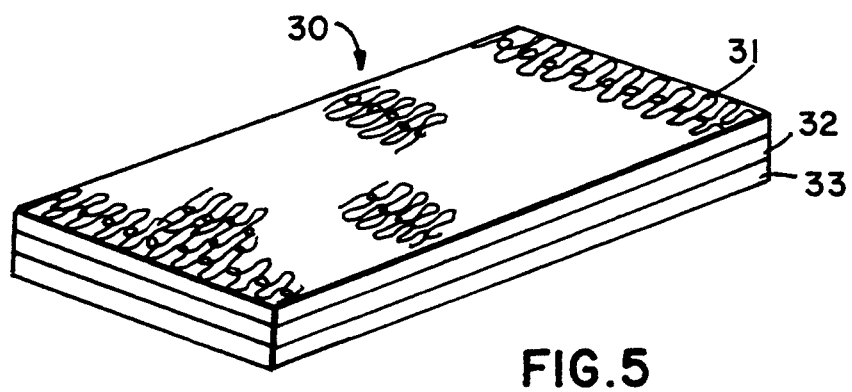
FIG. 5 depicts an alternative embodiment of apparatus for generating electrical currents in accordance with this invention.

FIG. 5 discloses an alternative embodiment to the open-ended, closed wall, generally cylindrical structure of FIG. 1 in the form of a planar electrical generator 30. The generator 30 comprises a foraminous electrode 31, an intermediate insulator 32 and a second foraminous electrode 33. The electrodes 31 and 33 have different electrochemical potentials and are compatible in the environment. If such a structure 30 is placed proximate a tumor or other portion of the body subject to hyperplastic cell growth in a flat orientation or conforming to the form of the tumor or region of hyperplastic cell growth, electrolytes (typically blood) in surrounding vessels will permeate the materials and increase the effectiveness of electrolysis. The foraminous nature of the electrodes 31 and 33 and the insulating membrane 32 also facilitate the transfer of hyperplastic cells past the electrodes to form a conductive bridge and initiate current flow.

There have been disclosed specific embodiments of apparatus for the in situ generation of an electrical current in a biological environment in accordance with this invention, particularly one characterized by the actual or potential presence of hyperplastic cells. Each generator comprises electrodes having different electrochemical potentials that are separated by an insulating member. Fluids at the generator site constitute an electrolyte and hyperplastic cells that bridge the electrodes produce a current path. Electrolytic action then generates an electric current that passes through the current path and impedes hyperplastic cell growth. It has been observed that this current can terminate cell growth of a tumor proximate the generator.

One particular embodiment comprises an electrolytic stent having inner and outer open mesh stents formed of different metals and an intermediate foraminous insulating member that separates the two metallic stents. This stent is particularly adapted for use in a vessel proximate a tumor. Fluid in the vessel acts as an electrolyte and tumor cells transporting across stent walls provide a current path. The resulting current prevents the formation of micro tumors that otherwise could partially or fully occlude the vessel.

It will be apparent that a number of variations and modifications can be made to the specifically disclosed structures without departing from the true spirit and scope of this invention. The disclosure, for example, has described criteria for the selection of particular elements and has described specific materials that are adapted for use in humans. In other applications different elements can be used. There are disclosed apparatus in cylindrical and planar form; other forms can be used. Any or all of the specifically disclosed foraminous electrodes and insulators can be replaced by solid structures in other applications. Each such embodiment, however, will still be characterized by two electrodes of differing electrochemical potential and an intermediate insulator that isolates the electrodes from each other and will be constructed in accordance with this invention. Therefore, it is the intent of the appended claims to cover all such variations and modifications as come within the true spirit and scope of this invention.

What is claimed as new and desired to be secured by Letters Patent of the United States is:

1. Apparatus for the in situ generation of an electrical current in a biological environment including electrically conductive tissue and an electrolyte, said current generation apparatus comprising first and second layers of electrically conductive materials of different electrochemical potentials and an insulating third layer intermediate and contiguous said first and second layers, each of said layers having a passage therethrough into which proximate conductive tissue cells can expand to bridge said first and second layers, whereby said apparatus, when immersed in the electrolyte, generates electrolytically an electrical current through the bridging conductive tissue cells.

2. Apparatus for the in situ generation of electrical current as recited in claim 1 wherein each of the materials of said first, second and third layers are selected from a group that are compatible with the biological environment including the conductive tissue and the electrolytes.

3. Apparatus for the in situ generation of electrical current as recited in claim 2 wherein said first and second layers are materials selected from the group consisting of iron, tantalum and silver and an aluminum magnesium alloy.

4. Apparatus for the in situ generation of electrical current as recited in claim 3 wherein said first and second layers are formed of iron and tantalum respectively.

5. Apparatus for the in situ generation of electrical current as recited in claim 3 wherein said first and second layers are formed of silver and tantalum respectively.

6. Apparatus for the in situ generation of electrical current as recited in claim 3 wherein said first and second layers are formed of an aluminum magnesium alloy and tantalum respectively.

7. Apparatus for the in situ generation of electrical current as recited in claim 2 wherein said insulating layer is inert in the biological environment.

8. Apparatus for the in situ generation of electrical current as recited in claim 7 wherein said insulating layer is a polymer.

9. Apparatus for the in situ generation of electrical current as recited in claim 7 wherein said conductive layers and insulating layer are foraminous and collectively form a permeable membrane.

10. Apparatus for the in situ generation of electrical current as recited in claim 2 wherein said first, second and third layers collectively form a planar apparatus.

11. Apparatus for the in situ generation of electrical current as recited in claim 2 wherein said first, second and third layers collectively form a substantially tubular structure.

12. Apparatus for the in situ generation of electrical current as recited in claim 11 wherein at least one of said first and second layers provides a self-supporting structure.

13. A stent assembly for insertion in a vessel having a boundary vessel wall with tissue cells and containing an electrolytic fluid comprising, as a nested structure:
A. an inner stent formed of a conductive material with a first electrochemical potential,
B. an outer stent formed of a conductive material with a second electrochemical potential that differs from the first electrochemical potential, and
C. an intermediate insulating means for electrically isolating said inner and outer stents from each other, said stent assembly, in a vessel, having a passage therethrough into which proximate conductive cells can expand, and forming an electrolytic generator when the electrolytic fluid in the vessel contacts said stent assembly and when the conductive tissue cells form a conductive path bridging said inner and outer stents.

14. A stent assembly as recited in claim 13 wherein said stents are composed from materials selected from the group consisting of aluminum, silver, iron, tantalum and alloy of aluminum magnesium.

15. A stent assembly as recited in claim 14 wherein one of said stents is formed of iron and the other of said stents is formed of tantalum whereby said tantalum comprises a cathode and said iron comprises an anode.

16. A stent assembly as recited in claim 14 wherein one of said stents is formed of silver and the other of said stents is formed of tantalum whereby said tantalum comprises a cathode and said silver comprises an anode.

17. A stent assembly as recited in claim 14 wherein one of said stents is formed of a tantalum filament in an open mesh, self-supporting structure.

18. A stent assembly as recited in claim 14 wherein said insulating layer is composed of a polymer.

19. A stent assembly as recited in claim 14 wherein said insulating means is composed of polyethylene.

20. A stent assembly as recited in claim 13 wherein each of said stents and insulating means are foraminous.

21. A method for generating current for transfer through hyperplastic cells that form proximate a vessel in an environment including an electrolytic fluid comprising the step of positioning in the vessel a multiple layer structure having first and second layers of electrically conductive mesh formed of materials of different electrochemical potentials that are insulated from one another, and enabling the hyperplastic cells to bridge the layers in the presence of electrolytic fluid thereby generating an electrical current through the bridge that impedes the growth of the hyperplastic cells.

22. A method as recited in claim 21 wherein the multiple layer structure comprises multiple sheets, said method additionally comprising the steps of locating the sheets proximate existent hyperplastic cells and forming the sheets to conform the multiple layer structure to the profile of the hyperplastic cells.

23. A method as recited in claim 21 wherein the first and second layers are formed of concentric tubular structures separated by a tubular insulating member, said method additionally comprising locating the multi-layer structure in tubular form at the walls of the vessel.

24. A method as recited in claim 23 wherein at least one of the layers is formed of loosely interlocked knitted loops of a metal filament and said multi-layer structure is adapted for being compacted to a small radial size for introduction lengthwise into the vessel, said method additionally comprising the step of expanding the multi-layer structure to engage the vessel walls.

25. Apparatus for the in situ generation of an electrical current in an electrically conductive biological environment with an electrolyte, said current generation apparatus comprising first and second foraminous layers of electrically conductive materials of different electrochemical potentials and a foraminous insulating third layer intermediate said first and second layers whereby said first and second layers, when immersed in the electrolyte become coupled conductively to the biological environment and generate electrolytically an electrical current for transfer through the biological environment.

26. Apparatus for the in situ generation of electrical current as recited in claim 25 wherein each of the materials of said first, second and third layers are selected from a group that are compatible with the biological environment and the electrolytes in that environment.

27. Apparatus for the in situ generation of electrical current as recited in claim 25 wherein said first and second layers are materials selected from the group consisting of iron, tantalum and silver and an aluminum magnesium alloy.

28. Apparatus for the in situ generation of electrical current as recited in claim 27 wherein said first and second layers are formed of iron and tantalum respectively.

29. Apparatus for the in situ generation of electrical current as recited in claim 27 wherein said first and second layers are formed of silver and tantalum respectively.

30. Apparatus for the in situ generation of electrical current as recited in claim 27 wherein said first and second layers are formed of an aluminum magnesium alloy and tantalum respectively.

31. Apparatus for the in situ generation of electrical current as recited in claim 27 wherein said insulating layer is inert in the biological environment.

32. Apparatus for the in situ generation of electrical current as recited in claim 31 wherein said insulating layer is a polymer.

33. Apparatus for the in situ generation of electrical current as recited in claim 25 wherein said first, second and third layers collectively form a planar apparatus.

34. Apparatus for the in situ generation of electrical current as recited in claim 25 wherein said first, second and third layers collectively form a substantially tubular wall structure.

35. Apparatus for the in situ generation of electrical current as recited in claim 34 wherein at least one of said first and second layers provides a self-supporting structure.

* * * * *